US00PP24820P2

(12) United States Plant Patent
Wood

(10) Patent No.: US PP24,820 P2
(45) Date of Patent: Aug. 26, 2014

(54) ***HYDRANGEA* PLANT NAMED 'MAK20'**

(50) Latin Name: *Hydrangea serrata*
Varietal Denomination: MAK20

(71) Applicant: Timothy D. Wood, Spring Lake, MI (US)

(72) Inventor: Timothy D. Wood, Spring Lake, MI (US)

(73) Assignee: Spring Meadow Nursery, Inc, Grand Haven, MI (US)

( * ) Notice: Subject to any disclaimer, the term of this patent is extended or adjusted under 35 U.S.C. 154(b) by 92 days.

(21) Appl. No.: 13/573,841

(22) Filed: Oct. 8, 2012

(51) Int. Cl.
*A01H 5/00* (2006.01)

(52) U.S. Cl.
USPC ..... Plt./250

(58) Field of Classification Search
USPC ..... Plt./250
See application file for complete search history.

*Primary Examiner* — Annette Para
(74) *Attorney, Agent, or Firm* — C. A. Whealy

(57) ABSTRACT

A new and distinct cultivar of *Hydrangea* plant named 'MAK20', characterized by its upright to outwardly spreading and mounding plant habit; strong and sturdy stems; dark green-colored leaves; large lacecap-type inflorescences with intense pink and yellow green-colored sterile flowers; remontant flowering habit; and good garden performance.

2 Drawing Sheets

Botanical designation: *Hydrangea serrata.*
Cultivar denomination: 'MAK20'.

BACKGROUND OF THE INVENTION

The present invention relates to a new and distinct cultivar of *Hydrangea* plant, botanically known as *Hydrangea serrata* and hereinafter referred to by the name 'MAK20'.

The new *Hydrangea* plant is a product of a planned breeding program conducted by the Inventor in Grand Haven, Mich. The objective of the breeding program was to develop new hardy *Hydrangea* plants with strong stems and attractive foliage and flower coloration.

The new *Hydrangea* plant originated from an open-pollination in 2005 of the *Hydrangea serrata* 'Maiko', not patented, as the female, or seed parent and an unknown selection of *Hydrangea serrata* as the male, or pollen, parent. The new *Hydrangea* plant was discovered and selected by the Inventor in 2009 as a single flowering plant within the progeny of the stated open-pollination in a controlled environment in Grand Haven, Mich.

Asexual reproduction of the new cultivar by softwood cuttings in a controlled environment in Grand Haven, Mich. since June, 2009 has shown that the unique features of this new *Hydrangea* plant are stable and reproduced true to type in successive generations of asexual reproduction.

SUMMARY OF THE INVENTION

Plants of the new *Hydrangea* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'MAK20'. These characteristics in combination distinguish 'MAK20' as a new and distinct *Hydrangea* plant:

1. Upright to outwardly spreading and mounding plant habit.
2. Strong and sturdy stems.
3. Dark green-colored leaves.
4. Large lacecap-type inflorescences with intense pink and yellow green-colored sterile flowers.
5. Remontant flowering habit.
6. Good garden performance.

Plants of the new *Hydrangea* differ from plants of the female parent, 'Maiko', in the following characteristics:

1. Plants of the new *Hydrangea* are taller than plants of 'Maiko'.
2. Plants of the new *Hydrangea* have larger inflorescences than plants of 'Maiko'.
3. Plants of the new *Hydrangea* have lacecap-type inflorescences whereas plants of 'Maiko' have inflorescences that are between lacecap to mophead-types.

Plants of the new *Hydrangea* can be compared to plants of *Hydrangea serrata* 'Lynn', disclosed in U.S. Plant Pat. No. 20,019. In side-by-side comparisons, plants of the new *Hydrangea* differ from plants of 'Lynn' in the following characteristics:

1. Plants of the new *Hydrangea* are more mounding than and not as upright as plants of 'Lynn'.
2. Leaves of plants of the new *Hydrangea* are not as glossy as leaves of plants of 'Lynn'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of a typical flowering plant of 'MAK20' grown in a container.

The photograph on the second sheet is a close-up view of a typical flowering plant of 'MAK20'.

DETAILED BOTANICAL DESCRIPTION

Plants used for the aforementioned photographs and the following description were grown during the summer in 5-gallon containers in an outdoor nursery in Grand Haven, Mich. and under cultural practices which closely approximate commercial *Hydrangea* production. Plants of the new *Hydrangea* were three years old when the photographs and description were taken. In the following description, color references are made to The Royal Horticultural Society Colour Chart, 2001 Edition, except where general terms of ordinary dictionary significance are used.

Botanical description: *Hydrangea serrata* 'MAK20'.

Parentage:

*Female, or seed, parent.*—*Hydrangea serrata* 'Maiko', not patented.

*Male, or pollen, parent.*—Unknown selection of *Hydrangea serrata*, not patented.

Propagation:

*Type cutting.*—By softwood cuttings.

*Time to initiate roots, summer.*—About ten days at temperatures of about 20° C.

*Time to produce a rooted young plant, summer.*—About one month at temperatures of about 20° C.

*Root description.*—Fine to thick, fibrous; white and brown in color.

*Rooting habit.*—Freely branching; dense.

Plant description:

*Plant form and growth habit.*—Perennial deciduous shrub; upright to outwardly spreading and mounding plant habit; broad inverted triangle; strong and sturdy lateral branches; freely basal branching habit with about 20 lateral branches developing per plant; vigorous growth habit.

*Plant height.*—About 65 cm.

*Plant diameter or area of spread.*—About 90 cm.

*Lateral branches.*—Length: About 60 cm to 70 cm. Diameter, towards the base of the plant: About 1 cm to 1.2 cm. Diameter, towards the apex of the plant: About 3 mm. Internode length, towards the base of the plant: About 10 cm. Internode length, towards the apex of the plant: About 1.5 cm. Strength: Strong, sturdy. Texture: Smooth, glabrous; longitudinally ridged. Aspect: Erect to about 85° from vertical. Color: Between 144B and 145B with random flecks, close to 187A.

Foliage description:

*Arrangement.*—Opposite, simple.

*Length.*—About 14 cm to 16.5 cm.

*Width.*—About 9.5 cm to 11.5 cm.

*Shape.*—Elliptic to ovate.

*Apex.*—Acuminate.

*Base.*—Attenuate.

*Margin.*—Deeply serrate.

*Texture, upper and lower surfaces.*—Rugose; glabrous.

*Luster, upper and lower surfaces.*—Dull to slightly glossy.

*Venation pattern.*—Pinnate.

*Color.*—Developing leaves, upper surface: Darker than 137A. Developing leaves, lower surface: Close to 146B. Fully expanded leaves, upper surface: Darker than 139A; venation, close to 144B variably tinged with red purple. Fully expanded leaves, lower surface: Close to 137A; venation, close to 144A.

*Petioles.*—Length: About 3 cm to 3.5 cm. Diameter: About 3.5 mm. Texture, upper and lower surfaces: Smooth, glabrous. Color, upper surface: Close to 144B variably tinged with red purple. Color, lower surface: Close to 144A.

Flower description:

*Flower type and habit.*—Sterile and fertile flowers arranged on large terminal and axillary lacecap-type cymes; inflorescences upright and individual flowers face upright to outwardly.

*Fragrance, fertile flowers.*—Slightly fragrant, pleasant.

*Fragrance, sterile flowers.*—None detected.

*Natural flowering season.*—Flowering remontant from June to August in Grand Haven, Mich.

*Flower longevity, fertile flowers.*—Flowers last about four weeks on the plant; flowers not persistent.

*Flower longevity, sterile flowers.*—Flowers last about three months on the plant; flowers persistent.

*Quantity of flowers.*—Freely flowering; about 270 fertile flowers and about ten sterile flowers develop per inflorescence.

*Inflorescence height.*—About 5 cm to 6 cm.

*Inflorescence diameter.*—About 14 cm to 16 cm.

*Flower diameter, fertile flowers.*—About 8 mm.

*Flower depth (height), fertile flowers.*—About 3 mm.

*Flower diameter, sterile flowers.*—About 4 cm to 4.5 cm.

*Flower depth (height), sterile flowers.*—About 5 mm.

*Flower buds, fertile and sterile flowers.*—Length: About 3 mm. Diameter: About 3 mm. Shape: Orbicular. Color: Close to 146C.

*Petals, fertile flowers only.*—Arrangement: Five in a single whorl. Length: About 4 mm. Width: About 2 mm. Shape: Elliptic. Apex: Acuminate. Base: Attenuate. Margin: Entire. Texture, upper and lower surfaces: Smooth, glabrous. Color: When opening and fully opened, upper surface: Close to 74C. When opening and fully opened, lower surface: Close to 74D.

*Sepals, fertile flowers.*—Quantity per flower: Five in a single whorl. Length: About 4 mm. Width: About 4 mm. Apex: Acute. Margin: Entire. Texture, upper and lower surfaces: Smooth, glabrous. Color, upper and lower surfaces: Close to 155B.

*Sepals, sterile flowers.*—Quantity per flower: About four or five in a single whorl. Length: About 2 cm to 2.2 cm. Width: About 2.4 cm to 2.7 cm. Shape: Oval. Apex: Obtuse. Base: Attenuate. Margin: Serrate. Texture, upper and lower surfaces: Smooth, glabrous. Color: When opening and fully opened, upper surface: Close to 67B; towards the base, close to 154A; venation, light yellow green. When opening and fully opened, lower surface: Close to 63D; venation, close to 67B.

*Pedicels, fertile flowers.*—Length: About 2.5 cm to 3.5 cm. Diameter: About 3 mm. Strength: Strong. Aspect: Erect to about 45° from stem axis. Texture: Smooth, glabrous. Color: Close to 177A.

*Pedicels, sterile flowers.*—Length: About 1 cm to 1.5 cm. Diameter: About 1.5 mm. Strength: Strong. Aspect: About 45° to 90° from stem axis. Texture: Smooth, glabrous. Color: Close to 67A.

*Reproductive organs, fertile flowers only*.—Stamens: Quantity per flower: About ten to twelve. Anther shape: Oblong. Anther length: Less than 1 mm. Anther color: Close to 66C. Pollen amount: Moderate. Pollen color: Yellowish white. Pistils: Pistil quantity per flower: About four, fused. Pistil length: About 4 mm to 5 mm. Stigma shape: Rounded. Stigma color: Close to 66D. Style length: About 1.4 mm. Style color: Close to 66D. Ovary color: Close to 66D.

*Seeds*.—Quantity per inflorescence: Numerous. Size: Dust-like, less than 0.1 mm by less than 0.1 mm. Color: Brown.

Disease & pest resistance: Plants of the new *Hydrangea* have been observed to be tolerant to Downey Mildew. Plants of the new *Hydrangea* have not been observed to be resistant to pests or other pathogens common to *Hydrangea* plants.

Garden performance: Plants of the new *Hydrangea* have been observed to have good garden performance and to tolerate wind, rain and temperatures ranging from about −25° C. to about 37° C.

It is claimed:

1. A new and distinct *Hydrangea* plant named 'MAK20' as illustrated and described.

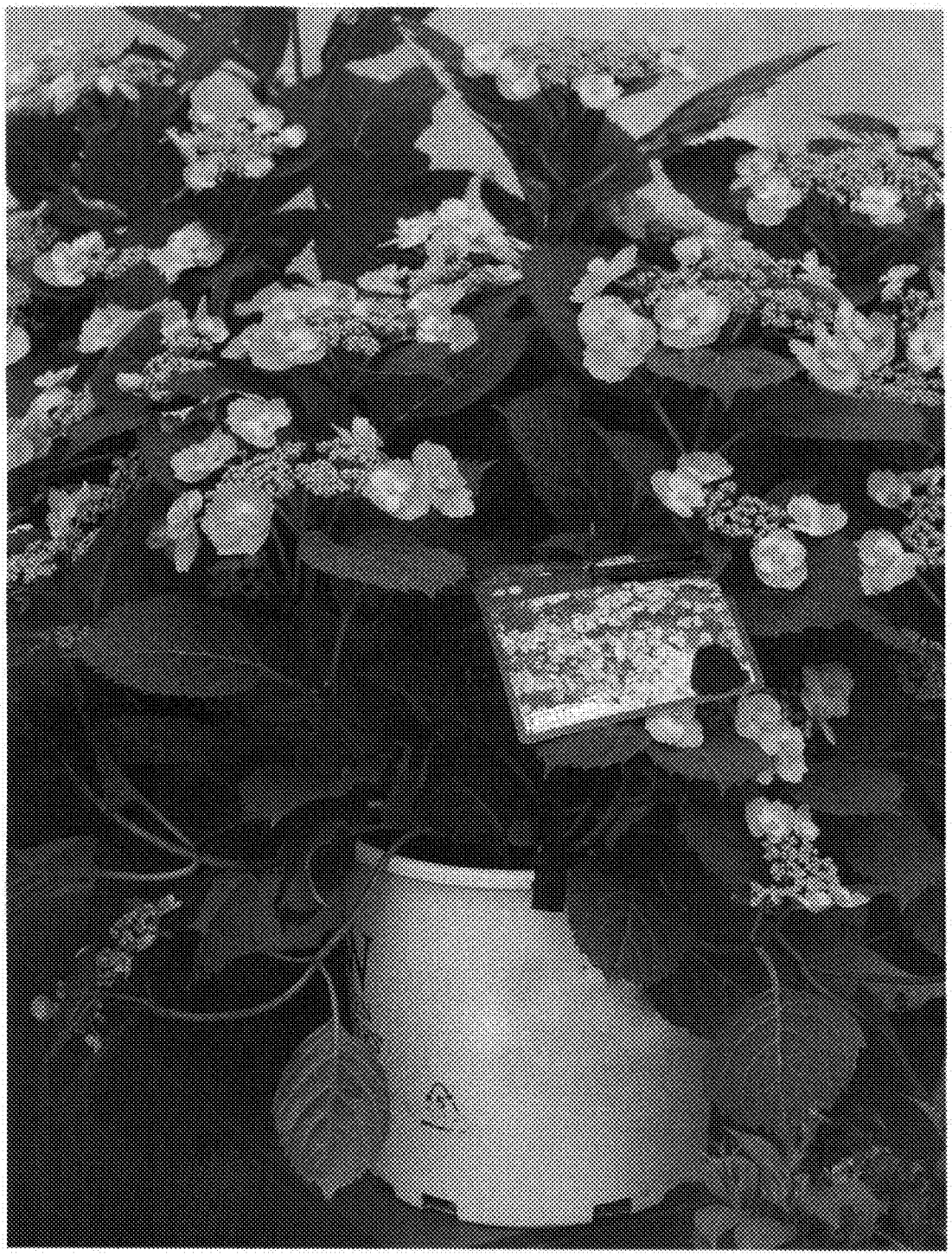

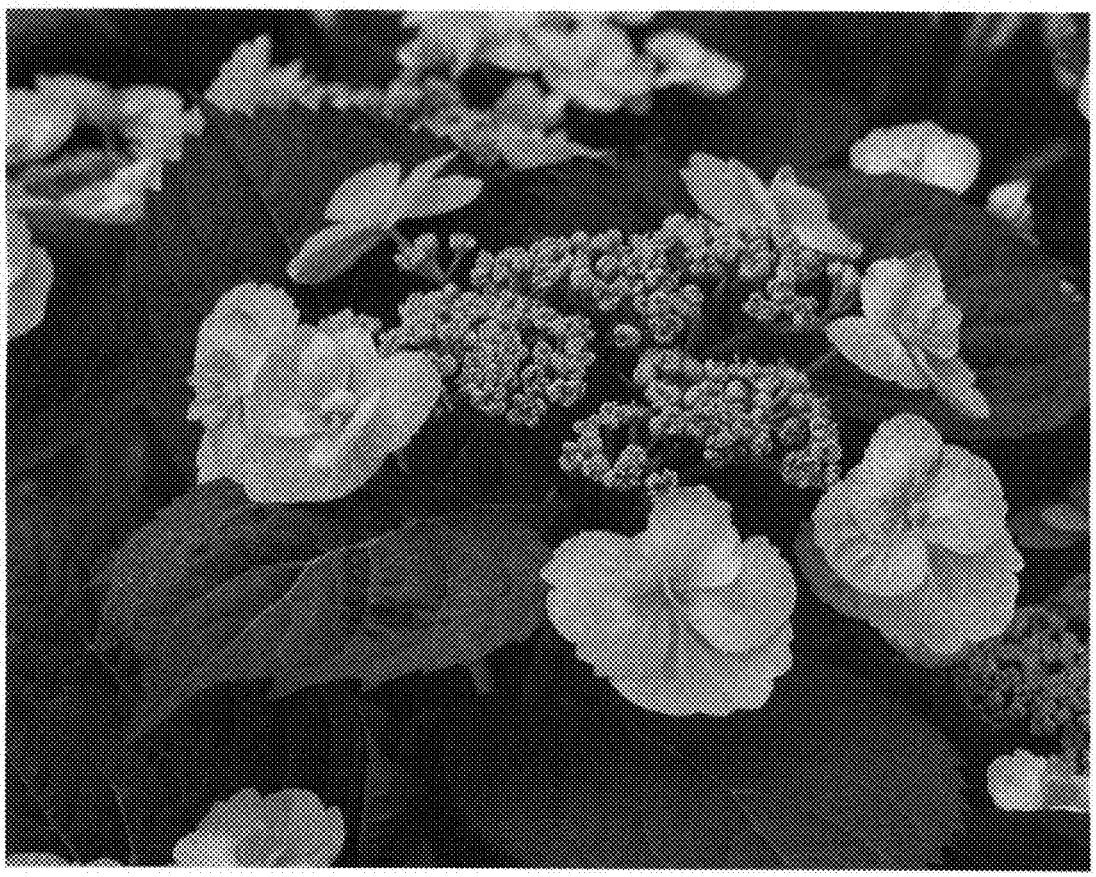

* * * * *